US012565652B1

(12) United States Patent
Thompson

(10) Patent No.: US 12,565,652 B1
(45) Date of Patent: Mar. 3, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/092,603

(22) Filed: Mar. 27, 2025

(51) Int. Cl.
*C12N 15/86* (2006.01)
*C12N 15/113* (2010.01)

(52) U.S. Cl.
CPC .......... *C12N 15/1135* (2013.01); *C12N 15/86* (2013.01); *C12N 2310/141* (2013.01); *C12N 2750/14142* (2013.01)

(58) Field of Classification Search
None
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 * | 11/2021 | Minshull | C12N 9/1241 |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |
| 12,195,747 B1 | 1/2025 | Thompson | |
| 12,281,309 B1 | 4/2025 | Thompson | |
| 2020/0362344 A1 | 11/2020 | Minshull et al. | |
| 2024/0026377 A1 | 1/2024 | Thompson | |

FOREIGN PATENT DOCUMENTS

CA        2721333 A1    10/2009

OTHER PUBLICATIONS

Kondratov et al. Molecular Therapy, 2017, vol. 25, No. 12, pp. 2661-2675.. (Year: 2017).*
Wang, et al. Nat Rev Drug Discov. May 2019;18(5):358-378. (Year: 2019).*
O'Brien et al. Frontiers in Endocrinology, vol. 9, Aug. 3, 2018. (Year: 2018).*
Zhang et al. Drug Design, Development and Therapy, Published Feb. 22, 2021, pp. 721-733. (Year: 2021).*
Gorski, S., Vogel, J. & Doudna, J., Nat Rev Mol Cell Biol 18, 215-228. (Year: 2017).*
Van den Berg, et al. pp. 1-12, Molecular Therapy, Nucleic Acids, vol. 5, 2016. (Year: 2016).*
Bottoni et al. "Targeting BTK through microRNA in chronic lymphocytic leukemia." Blood, The Journal of the American Society of Hematology 128.26 (2016): 3101-3112.

O'Brien et al. Overview of MicroRNA Biogenesis, Mechanisms of Actions, and Circulation, Frontiers in Endocrinology, vol. 9, Article 402: 1-12 (2018). (Year: 2018).
Gorski, S., Vogel, J. & Doudna, J. RNA-based recognition and targeting: sowing the seeds of specificity. Nat Rev Mol Cell Biol 18, 215-228 (2017). (Year: 2017).
Brutons Tyrosine Kinase Genbank Sequen (2023).
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Denzler R et al. Impact of MicroRNA Levels, Target-Site Complementarity, and Cooperativity on Competing Endogenous RNA-Regulated Gene Expression. Mol Cell. Nov. 3, 2016;64(3):565-579. doi: 10.1016/j.molcel.2016.09.027 (Year: 2016).
Gen Bank EGF Sequence (2023).
Nature (2010. Gene Expression, Scitable, Available online at Nature. com) <https://www.nature.com/scitable/topicpage/gene-expression-14121669> (2010).
Tritschler et al. "Concepts and limitations for learning developmental trajectories from single cell genomics." Development 146.12 (2019): dev170506.
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI Search results for SEQ ID No. 5 2024.
NCBI Nucleotide Sequence ALK Lingand, search performed Dec. 26, 2024 (2023).
NCBI Nucleotide Sequence ALK Receptor, search performed Dec. 26, 2024 (2023).
GenBank EGFR Sequence (2023).
Genbank FLT3 Sequence (2024).
NCBI Nucleotide Sequence for PARP, search performed Dec. 26, 2024 (2024).
Ying (et al. 2008, The MicroRNA (miRNA): Overview of the RNA Genes that Modulate Gene Function, Mol, Biotechnol. 38:257-268) (Year: 2008).
Pagliuca (et al. 2013. Analysis of the combined action of miR-143 and miR-145 on oncogenic pathways in colorectal cancer cells reveals a coordinate program of gene repression. Oncogene 32:4806-4813) (Year: 2013).
Lam (et al. 2015. siRNA Versus miRNA as Therapeutics for Gene Silencing, Molec. Ther. Nuc. Ac. 4:e252) (Year: 2015).

(Continued)

*Primary Examiner* — Ram R Shukla
*Assistant Examiner* — Jeffrey Mark Sifford
(74) *Attorney, Agent, or Firm* — Gowling WLG (Canada) LLP

(57) ABSTRACT

The embodiments of the present disclosure relate to decreasing the bioavailability of one or more target biomolecules by providing a composition that comprises a recombinant plasmid with one or more sequences of micro interfering ribonucleic acid (miRNA). When the recombinant plasmid interacts with a target cell, it causes the target cell to upregulate production of the miRNA, which then decreases the bioavailability of the target biomolecule. In some embodiments of the present disclosure, the target biomolecule is a kinase.

2 Claims, No Drawings

Specification includes a Sequence Listing.

(56)             References Cited

OTHER PUBLICATIONS

Fattore (et al. 2016. miR-579-3p controls melanoma progression and resistance to target therapy. PNAS 113 [34]:E5005-E5013) (Year: 2016).

Origene (2024. Product datasheet for SC207797 B Raf [BRAF] [NM_004333] Human 3' UTR Clone. Rockville, MD: Origene) (Year:2024).

NCBI (*Homo sapiens* B-Raf proto-oncogene, serine/threonine kinase [BRAF], transcript variants 1-2. 4-14, mRNA: [see reference for NM number]. Available online at NCBI.nlm.nih.gov. Accessed on May 16, 2025 (Year: 2025).

MiRbase (2025, "miR-143" and "miR-145", and "miR-579-3p". Available online at miRbase.org. Accessed on May 16, 2025) (Year: 2025).

*Homo sapiens* VEGF, mRNA, NCBI Reference Sequence, version Oct. 2023, 9 pages, retrieved from the internet Jul. 2, 2025 (Year: 2023).

Kenji and Mizukami < star-protocols.cell.com/protocols/3185 >, Dec. 15, 2023, 17 pages, accessed on 9/9/20225 (Year: 2023).

Lundstrom K., Viruses. Mar. 7, 2023;15(3):698 (Year: 2023).

Wallace JA et al., Blood, Apr. 21, 2017;129(23):3074-3086 (Year: 2017).

* cited by examiner

COMPOSITION FOR REGULATING PRODUCTION OF INTERFERING RIBONUCLEIC ACID

CROSS REFERENCE TO RELATED APPLICATION

The present application is a continuation of U.S. patent application Ser. No. 18/932,078 filed Oct. 30, 2024, entitled "Composition For Regulating Production Of Interfering Ribonucleic Acid", currently pending, which is a division of U.S. patent application Ser. No. 18/518,069 filed Nov. 22, 2023, entitled "Composition For Regulating Production Of Interfering Ribonucleic Acid" currently pending, the entirety of which is incorporated herein by reference.

SEQUENCE LISTING

This application contains a Sequence Listing electronically submitted via Patent Center to the United States Patent and Trademark Office as an XML Document file entitled "A8149358US—Sequence Listing.xml" created on 2023 Nov. 17 and having a size of 75,546 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA that will suppress over-expression or mis-expression of kinases.

BACKGROUND

Bioactive molecules, including kinases, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro interfering ribonucleic acid (miRNA). The sequences of miRNA may be complimentary to a sequence of target messenger RNA (mRNA) that encodes for translation of a target biomolecule and the miRNA can cause the bioavailability of the target mRNA to decrease because it is degraded or inactivated by the miRNA, thereby causing a decrease in bioactivity of the target biomolecule within a subject that is administered the one or more compositions. In some embodiments of the present disclosure, the target biomolecule is a kinase. In some embodiments of the present disclosure, the target biomolecule is a kinase such as Bruton's tyrosine kinase. In some embodiments of the present disclosure, the target biomolecule is a kinase such as epidermal growth factor (EGF). In some embodiments of the present disclosure, the target biomolecule is a kinase such as vascular endothelial growth factor (VEGF). In some embodiments of the present disclosure, the target biomolecule is a kinase such as B-Raf. In some embodiments of the present disclosure, the target biomolecule is a kinase such as anaplastic lymphoma kinase (ALK). In some embodiments of the present disclosure, the target biomolecule is a kinase such as human epidermal growth factor receptor (HER). In some embodiments of the present disclosure, the target biomolecule is a kinase such as Fms-like tyrosine kinase 3 (FLT3). In some embodiments of the present disclosure, the target biomolecule is a kinase such as poly-ADP ribose polymerase (PARP).

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of Bruton's tyrosine kinase.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets mRNA of EGF.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets mRNA of VEGF.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets mRNA of BRAF.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets mRNA of ALK.

Some embodiments of the present disclosure relate to a recombinant plasmid. In some embodiments of the present disclosure, the RP comprises a nucleotide sequence of SEQ ID NO. 1 and SEQ ID NO. 7. The RP comprises a nucleotide sequence encoding one or more nucleotide sequences encoding a miRNA sequence that targets mRNA of HER.

Some embodiments of the present disclosure relate to a recombinant plasmid. In some embodiments of the present disclosure, the RP comprises a nucleotide sequence of SEQ ID NO. 1 and SEQ ID NO. 8. The RP comprises a nucleotide sequence encoding one or more nucleotide sequences encoding a miRNA sequence that targets mRNA of FLT3.

Some embodiments of the present disclosure relate to a recombinant plasmid. In some embodiments of the present disclosure, the RP comprises a nucleotide sequence of SEQ ID NO. 1 and SEQ ID NO. 9. The RP comprises a nucleotide sequence encoding one or more nucleotide sequences encoding a miRNA sequence that targets mRNA of PARP.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, SEQ ID NO. 6, SEQ ID NO. 7, SEQ ID NO. 8, or SEQ ID NO. 9, to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example Bruton's tyrosine kinase. A first approach utilizes gene vectors containing nucleotide sequences for increasing the endogenous production of one or more sequences of miRNA, which are complete or partial sequences and/or combinations thereof, that target and silence the mRNA of Bruton's tyrosine kinase, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example EGF. A first approach utilizes gene vectors containing nucleotide sequences for increasing the endogenous production of one or more sequences of miRNA, which are complete or partial sequences and/or combinations thereof, that target and silence the mRNA of EGF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example VEGF. A first approach utilizes gene vectors containing nucleotide sequences for increasing the endogenous production of one or more sequences of miRNA, which are complete or partial sequences and/or combinations thereof, that target and silence the mRNA of VEGF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example BRAF. A first approach utilizes gene vectors containing nucleotide sequences for increasing the endogenous production of one or more sequences of miRNA, which are complete or partial sequences and/or combinations thereof, that target and silence the mRNA of BRAF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example ALK. A first approach utilizes gene vectors containing nucleotide sequences for increasing the endogenous production of one or more sequences of miRNA, which are complete or partial sequences and/or combinations thereof, that target and silence the mRNA of ALK, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example HER. A first approach utilizes gene vectors containing nucleotide sequences for increasing the endogenous production of one or more sequences of miRNA, which are complete or partial sequences and/or combinations thereof, that target and silence the mRNA of HER, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example FLT3. A first approach utilizes gene vectors containing nucleotide sequences for increasing the endogenous production of one or more sequences of miRNA, which are complete or partial sequences and/or combinations thereof, that target and silence the mRNA of FLT3, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example PARP. A first approach utilizes gene vectors containing nucleotide sequences for increasing the endogenous production of one or more sequences of miRNA, which are complete or partial sequences and/or combinations thereof, that target and silence the mRNA of PARP, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a kinase that is found within a subject. A biomolecule may be endogenous or exogenous to a subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is Bruton's tyrosine kinase.

In some embodiments of the present disclosure, the target biomolecule is EGF.

In some embodiments of the present disclosure, the target biomolecule is VEGF.

In some embodiments of the present disclosure, the target biomolecule is BRAF.

In some embodiments of the present disclosure, the target biomolecule is ALK.

In some embodiments of the present disclosure, the target biomolecule is HER.

In some embodiments of the present disclosure, the target biomolecule is FLT3.

In some embodiments of the present disclosure, the target biomolecule is PARP.

In some embodiments of the present disclosure, the insert comprises one or more nucleotide sequences that each encode one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as Bruton's tyrosine kinase, EGF, VEGF, BRAF, ALK, HER, FLT3, or PARP. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as Bruton's tyrosine kinase, EGF, VEGF, BRAF, ALK, HER, FLT3, or PARP. Increased endogenous expression of the one or more miRNA sequences results in a decreased bioavailability of the desired biomolecule, which may also be referred to as a target biomolecule.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body mass. In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with examples being Bruton's tyrosine kinase, EGF, VEGF, BRAF, ALK, HER, FLT3, or PARP. The RP is comprised of AAV2 inverted terminal repeats (ITRs), a composite CASI promoter, a human growth hormone (HGH) signal peptide followed by a miRNA expression cassette containing up to six different miRNAs targeting Bruton's tyrosine kinase, EGF, VEGF, BRAF, ALK, HER, FLT3, or PARP, followed by a Woodchuck Hepatitis Virus post-transcriptional regulatory element (WPRE) and an SV40 polyA signal.

SEQ ID NO. 1 (backbone sequence No. 1):
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtatataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtccttcggccctc aatccagcggaccttccttcccgcggcctgctgccggctctgcggcctcttccgcgtcttcgccttcgccctcagacgagtcggatctccctt gggccgcctccccgcctaagcttatcgataccgtcgagatctaacttgtttattgcagcttataatggttacaaataaagcaatagcatcacaaa tttcacaaataaagcattttttttcactgcattctagttgtggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggctcccttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgttttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccgtagaaaagatcaaaggatcttct tgagatcctttttttctgcgcgtaatctgctgcttgcaaacaaaaaaaccaccgctaccagcggtggtttgtttgccggatcaagagctaccaac tcttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca -continued gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgaccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgaccTt atgggactttcctacttggcagtacatctacgtattagtcatcgctattaccatggtcgaggtgagccccacgttctgcttcactctccccatctc cccccctccccaccccaattttgtatttatttattttttaattattttgtgcagcgatggggggggggggggggggggcgcgcgccaggc ggggcggggggggcgaggggcggggggggcgaggcggagaggtgcggcggcagccaatcagagcggcgcgctccgaaagttt ccttttatggcgaggcggcggcggcggcggccctataaaaagcgaagcgcgcgggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttTctttTtTtTtTctacaggtcctgggtgacgaacagggtaccgccaccatggc caccggctctcgcacaagcctgctgctggctttcggactgctgtgcctgccttggctccaggagggctccgcc

3'

SEQ ID NO. 2 (miRNA expression cassette No. 2 - Bruton's tyrosine kinase):
5' gctagcatcgataccgtcgctatgtgctggaggcttgctgaaggctgtatgctgtaaggtggttatgggagaatgccgtttTggcctctgactg acggcattctcctaaccaccttacaggacacaaggcctgttactagcactcacatggaacaaatggcctctagcctggaggcttgctgaagg ctgtatgctgttgagtttcgcattcttgttgccgtttTtggcctctgactgacggcaacaagagcgaaactcaacaggacacaaggcctgttacta gcactcacatggaacaaatggcctctagcctggaggcttgctgaaggctgtatgctgtctatcctttcaagctagtcaccgtttTtggcctctgac tgacggtgactagcgaaggatagacaggacacaaggcctgttactagcactcacatggaacaaatggcctctctagaat

3'

SEQ ID NO. 3 (miRNA expression cassette No. 3 - EGFR):
5' gctagcatcgataccgtcgctatgtgctggaggcttgctgaaggctgtatgctgaagttagcatgtgtcccagaaccgtttTtggcctctgactg acggttctgggacatgctaacttcaggacacaaggcctgttactagcactcacatggaacaaatggcctctagcctggaggcttgctgaagg ctgtatgctgagaagaaaggtatcccaattgccgtttTtggcctctgactgacggcaattgggacctttcttctcaggacacaaggcctgttacta gcactcacatggaacaaatggcctctagcctggaggcttgctgaaggctgtatgctgtagtgtttccaaatactgcttgcgtttTtggcctctgac tgacgcaagcagtatggaaacactacaggacacaaggcctgttactagcactcacatggaacaaatggcctctctagaat

3'

SEQ ID NO. 4 (miRNA expression cassette No. 4 - VEGF):
5' gctagcatcgataccgtcgctatgtgctggaggcttgctgaaggctgtatgctgtctgacagtgatgtcatcctttcgtttTtggcctctgactgac gaaaggatgatcactgtcagacaggacacaaggcctgttactagcactcacatggaacaaatggcctctagcctggaggcttgctgaaggc tgtatgctgatttaggtcagatggaaactcgcgtttTtggcctctgactgacgcgagtttccctgacctaaatcaggacacaaggcctgttacta gcactcacatggaacaaatggcctctagcctggaggcttgctgaaggctgtatgctgagtgtatgcttaacgtggacttcgtttTtggcctctga ctgacgaagtccacgaagcatacactcaggacacaaggcctgttactagcactcacatggaacaaatggcctctctagaat

3'

-continued

SEQ ID NO. 5 (miRNA expression cassette No. 5 - BRAF):
5' gctagcatcgataccgtcgctatgtgctggaggcttgctgaaggctgtatgctgatacttcagcctgaatcgtgaccgttttggcctctgactg acggtcacgattggctgaagtatcaggacacaaggcctgttactagcactcacatggaacaaatggcctctagcctggaggcttgctgaag gctgtatgctgacttcactcatattgttccactcgtttggcctctgactgacgagtggaacaatgagtgaagtcaggacacaaggcctgttact agcactcacatggaacaaatggcctctagcctggaggcttgctgaaggctgtatgctgtatattctacaaatcaccagggcgttttggcctctg actgacgccctggtgatgtagaatatacaggacacaaggcctgttactagcactcacatggaacaaatggcctctctagaat

3'

SEQ ID NO. 6 (miRNA expression cassette No. 6 - ALK):
5' gctagcatcgataccgtcgctatgtgctggaggcttgctgaaggctgtatgctgtataagtccagtgagaagaaggcgttttggcctctgact gacgccttcttctctggacttatacaggacacaaggcctgttactagcactcacatggaacaaatggcctctagcctggaggcttgctgaagg ctgtatgctgctatcatcaaatgagctgctgcgtttggcctctgactgacgcagcagctcttgatgatagtcaggacacaaggcctgttacta gcactcacatggaacaaatggcctctagcctggaggcttgctgaaggctgtatgctgaagactgctggaattctatggctgtttttggcctctg actgacgaccatagaatccagcagtctcaggacacaaggcctgttactagcactcacatggaacaaatggcctctctagaat

3'

SEQ ID NO. 7 (miRNA expression cassette No. 7 - HER):
5' gctagcatcgataccgtcgctatgtgctggaggcttgctgaaggctgtatgctgattagcactggtgatttccggctgttttggcctctgactga cgaccggaaatccagtgctaatcaggacacaaggcctgttactagcactcacatggaacaaatggcctctagcctggaggcttgctgaagg ctgtatgctgattgagtttcgcattcttgttgccgtttggcctctgactgacggcaacaagagcgaaactcaacaggacacaaggcctgttact agcactcacatggaacaaatggcctctagcctggaggcttgctgaaggctgtatgctgattgatcaggcaaacatagtcccgttttggcctct gactgacgggactatgtgcctgatcaatcaggacacaaggcctgttactagcactcacatggaacaaatggcctctctagaat

3'

SEQ ID NO. 8 (miRNA expression cassette No. 8 - FLT3):
5' gctagcatcgataccgtcgctatgtgctggaggcttgctgaaggctgtatgctgtctgatcgtggtgttatttgggcgttttggcctctgactga cgcccaaataaccacgatcagacaggacacaaggcctgttactagcactcacatggaacaaatggcctctagcctggaggcttgctgaag gctgtatgctgttgagtttcgcattcttgttgccgtttggcctctgactgacggcaacaagagcgaaactcaacaggacacaaggcctgttac tagcactcacatggaacaaatggcctctagcctggaggcttgctgaaggctgtatgctgtatcctcttataactcagcctccgttttggcctctg actgacggaggctgagataagaggatacaggacacaaggcctgttactagcactcacatggaacaaatggcctctctagaat

3'

SEQ ID NO. 9 (miRNA expression cassette No. 9 - PARP):
5' gctagcatcgataccgtcgctatgtgctggaggcttgctgaaggctgtatgctgtcgtactgacttgtaggtatgccgttttggcctctgactga cggcatacctaagtcagtacgtcaggacacaaggcctgttactagcactcacatggaacaaatggcctctagcctggaggcttgctgaagg ctgtatgctgactcctaatcaatagcttccaccgtttttggcctctgactgacggtggaagcttgattaggagtcaggacacaaggcctgttacta gcactcacatggaacaaatggcctctagcctggaggcttgctgaaggctgtatgctgaatatgcctttaagctttgctgcgttttggcctctgac tgacgcagcaaagcaaaggcatattcaggacacaaggcctgttactagcactcacatggaacaaatggcctctctagaat

3'

SEQ ID NO: 10 = SEQ ID NO: 1 + SEQ ID NO: 2
5' aatcaacctctggattacaaaatttgtgaaagattgactggtattcttaactatgttgctcctttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctccctt gggccgcctccccgcctaagcttatcgataccgtcgagatctaacttgtttattgcagcttataatggttacaaataaagcaatagcatcacaaa tttcacaaataaagcattttttttcactgcattctagttgtggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattctttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattccctttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacgggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggcctttttgctggccttttgctca catgttcttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgaccttttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaataggggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgaccTT atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatggggggggggggggggggggcgcgcgccaggc ggggcggggcggggcgaggggggggcggggcgaggcggagaggtgcggcggcagccaatcagagcggcgcgctccgaaagttt cctttttatggcgaggcggcggcggcggcggcccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtaaggtggttatgggagaatgccgtttttggcctctgactgacggcattctcctaacca ccttacaggacacaaggcctgttactagcactcacatggaacaaatggcctctagcctggaggcttgctgaaggctgtatgctgttgagtttc gcattcttgttgccgttttggcctctgactgacggcaacaagagcgaaactcaacaggacacaaggcctgttactagcactcacatggaaca aatggcctctagcctggaggcttgctgaaggctgtatgctgtctatcctttcaagctagtcaccgtttttggcctctgactgacggtgactagcga aaggatagacaggacacaaggcctgttactagcactcacatggaacaaatggcctctctagaat

3'

SEQ ID NO: 11 = SEQ ID NO: 1 + SEQ ID NO: 3
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacagggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggcctttccccgtcaagctctaaatcggggggctcccctttagggttccgatttagtgctttacggcacctcga ccccaaaaaacttgattagggtgatggttcacgtagtgggccatcgccctgatagacggtttttcgcccttttgacgttggagtccacgttctttta atagtggactcttgttccaaactggaacaacactcaaccctatctcggtctattctttttgatttataagggattttgccgatttcggcctattggttaa aaaatgagctgatttaacaaaaatttaacgcgaatttttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaattatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga -continued gcgcgcagagagggagtggccaactccatcactagggggttccttgtgtagttaatgattaacccgccatgctacttatctacgtagccatgctct aggacattgattattgactagtggagttccgcgttacataacttacggtaaatggccgcctggctgaccgcccaacgaccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccaccccaatttttgtatttatttattttttaattatttttgtgcagcgatgggggggggggggggggggcgcgcgccaggc ggggcggggcggggcgagggggggcggggcgaggcggagaggtgcggcggcagccaatcagagcggcgcgctccgaaagttt ccttttatggcgaggcggcggcggcggcggcccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggtttttctttccagagagcggaacaggcgaggaaaagtagtcccttctcggcgattctgcggagggatctccgtggg gcggtgaacgccgatgatgcctctactaaccatgttcatgtttctttttttttctacaggtcctgggtgacgaacaggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgaagttagcatgtgtcccagaaccgttttggcctctgactgacggttctgggacatgct aacttcaggacacaaggcctgttactagcactcacatggaacaaatggcctctagcctggaggcttgctgaaggctgtatgctgagaagaa aggtatcccaattgccgttttggcctctgactgacggcaattgggacctttcttctcaggacacaaggcctgttactagcactcacatggaaca aatggcctctagcctggaggcttgctgaaggctgtatgctgtagtgtttccaaatactgcttgcgttttggcctctgactgacgcaagcagtatg gaaacactacaggacacaaggcctgttactagcactcacatggaacaaatggcctctctagaat

3'

SEQ ID NO: 12 = SEQ ID NO: 1 + SEQ ID NO: 4
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacgcgcgaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccctttagggttccgatttagtgctttacggcacctcga ccccaaaaaacttgattagggtgatggttcacgtagtgggccatcgccctgatagacggttttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttgggggct -continued

```
tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcaccgtttgaatctttacctacacattactcaggcattgcatttaaaatatatgagggttctaaaaatttttatccttgcgttg aaataaaggcttctcccgcaaaagtattacagggtcataatgttttttggtacaaccgatttagctttatgctctgaggctttattgcttaatttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctattttttataggttaatgtcatgataataatggtttcttagacgtcaggtggcacttttcggggaaatgtgc gcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaataggggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatgggggggggggggggggggggcgcgcgccaggc ggggcggggcggggcgaggggggggcggggcgaggcggagaggtgcggcggcagccaatcagagcggcgcgctccgaaagttt cctttttatggcgaggcggcggcggcggcggccctataaaaagcgaagcgcgcggggggggagtcgctgcgcgctgccttcgcccc gtgccccgctccgccgccgcctcgcgccgcccgcccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccccagtatcagcagaaggacattttaggacgggacttgggt
``` gactctagggcactggttttctttccagagagcggaacaggcgaggaaaagtagtcccttctcggcgattctgcggagggatctccgtggg gcggtgaacgccgatgatgcctctactaaccatgttcatgttttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtctgacagtgatgtcatcctttcgttttggcctctgactgacgaaaggatgatcactgt cagacaggacacaaggcctgttactagcactcacatggaacaaatggcctctagcctggaggcttgctgaaggctgtatgctgatttaggtc agatggaaactcgcgttttggcctctgactgacgcgagtttccctgacctaaatcaggacacaaggcctgttactagcactcacatggaacaa atggcctctagcctggaggcttgctgaaggctgtatgctgagtgtatgcttaacgtggacttcgtttttggcctctgactgacgaagtccacgaa gcatacactcaggacacaaggcctgttactagcactcacatggaacaaatggcctctctagaat

3'

SEQ ID NO: 13 = SEQ ID NO: 1 + SEQ ID NO: 5
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttcgggactttcgctttccc cctccctattgccacgcgcgaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcgggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtgtgtttgtccaaactcatcaatgtatccttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggctcccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt -continued

```
ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgctttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccccccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgcccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccaccccaattttgtatttatttattttttaattattttgtgcagcgatggggggggggggggggggggcgcgcgccaggc ggggcggggggggcgaggggggggcggggcgaggcggagaggtgcggcggcagccaatcagagcggcgcgctccgaaagttt cctttttatggcgaggcggcggcggcggcggcccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccagtatcagcagaaggacatttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgatacttcagcctgaatcgtgaccgttttggcctctgactgacggtcacgattggctga agtatcaggacacaaggcctgttactagcactcacatggaacaaatggcctctagcctggaggcttgctgaaggctgtatgctgacttcactc atattgttccactcgtttttggcctctgactgacgagtggaacaatgagtgaagtcaggacacaaggcctgttactagcactcacatggaacaa
``` atggcctctagcctggaggcttgctgaaggctgtatgctgtatattctacaaatcaccagggcgttttggcctctgactgacgccctggtgatg tagaatatacaggacacaaggcctgttactagcactcacatggaacaaatggcctctctagaat

3'

SEQ ID NO: 14 = SEQ ID NO: 1 + SEQ ID NO: 6
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccccactggttggggcattgccaccacctgtcagctccttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcgggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactctttttactcggtggcctcactgattatataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggctcccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcaccggtttgaatctttacctacacattactcaggcattgcatttaaaatatatgaggggttctaaaaattttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc -continued agatggtaagccctcccgtatcgtagttatctacacgacggggagtcaggcaactatggatgaacgaaatagacagatcgctgagataggt gcctcactgattaagcattggtaactgtcagaccaagtttactcatatatacttttagattgatttaaaacttcattttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaccaccgctaccagcggtggtttgtttgccggatcaagagctaccaac tcttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttattttttaattattttgtgcagcgatgggggggggggggggggggggcgcgcgccaggc ggggggggcggggcgagggggggcggggcgaggcggagaggtgcggcggcagccaatcagagcggcgcgctccgaaagttt cctttatggcgaggcggcggcggcggcggccctataaaaagcgaagcgcgcggggggggagtcgctgcgcgctgccttcgcccc gtgccccgctccgccgccgcctcgcgccgccccgcccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtaacgccgatgatgcctctactaaccatgttcatgtttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtataagtccagtgagaagaaggcgtttttggcctctgactgacgccttcttctctggact tatacaggacacaaggcctgttactagcactcacatggaacaaatggcctctagcctggaggcttgctgaaggctgtatgctgctatcatcaa atgagctgctgcgttttggcctctgactgacgcagcagctcttgatgatagtcaggacacaaggcctgttactagcactcacatggaacaaat ggcctctagcctggaggcttgctgaaggctgtatgctgaagactgctggaattctatggctgtgttttggcctctgactgacgaccatagaatcc agcagtctcaggacacaaggcctgttactagcactcacatggaacaaatggcctctctagaat

3'

SEQ ID NO: 15 = SEQ ID NO: 1 + SEQ ID NO: 7
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtgggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccttttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgc ggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttaattta aaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca -continued catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgaccctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaataggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccaccccaattttgtatttatttatttttttaattattttgtgcagcgatggggggggggggggggggggcgcgcgccaggc ggggcggggcggggcgagggggggcggggcgaggcggagaggtgcggcggcagccaatcagagcggcgcgctccgaaagttt cctttttatggcgaggcggcggcggcggcggccctataaaaagcgaagcgcgcggggggggagtcgctgcgcgctgccttcgcccc gtgccccgctccgccgccgcctcgcgccgccccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccagtatcagcagaaggacattttaggacgggacttgggt gactctagggcactggtttttctttccagagagcggaacaggcgaggaaaagtagtcccttctcggcgattctgcggagggatctccgtggg gcggtaacgccgatgatgcctctactaaccatgttcatgtttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgattagcactggtgatttccggctgtttttggcctctgactgacgaccggaaatccagtg ctaatcaggacacaaggcctgttactagcactcacatggaacaaatggcctctagcctggaggcttgctgaaggctgtatgctgattgagttt cgcattcttgttgccgtttttggcctctgactgacggcaacaagagcgaaactcaacaggacacaaggcctgttactagcactcacatggaac aaatggcctctagcctggaggcttgctgaaggctgtatgctgattgatcaggcaaacatagtcccgtttttggcctctgactgacgggactatgt gcctgatcaatcaggacacaaggcctgttactagcactcacatggaacaaatggcctctctagaat

3'

SEQ ID NO: 16 = SEQ ID NO: 1 + SEQ ID NO: 8
5' aatcaacctctggattacaaaatttgtgaaagattgactggtattcttaactatgttgctccttttacgctatgtggatacgctgctttaatgcctttgt atcatgctattgcttcccgtatggctttcatttttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcattttttttcactgcattctagttgtggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctccctttagggttccgatttagtgctttacggcacctcga -continued

```
ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaatttttaacaaaatattaacgtttacaatttaaatatttgcttatacaatcttcctgttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcaccctgtttgaatctttacctacacattactcaggcattgcatttaaaatatatgagggttctaaaaatttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatgggaggcggataaagttgcaggaccactt ctgcgctcggcccttccggctggctggtttattgctgataaatctggagccggtgagcgtgggtctcgcggtatcattgcagcactggggcc agatggtaagccccccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttattttttaattatttttgtgcagcgatgggggggggggggggggggcgcgcgccaggc ggggcggggcggggcgagggggggcggggcgaggcgagaggtgcggcggcagccaatcagagcggcgcgctccgaaagttt ccttttatggcgaggcggcggcggcggcggcggccctataaaaagcgaagcgcgcggggggggagtcgctgcgcgctgccttcgcccc
```

-continued gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtctgatcgtggtgttatttgggcgtttttggcctctgactgacgcccaaataaccacgat cagacaggacacaaggcctgttactagcactcacatggaacaaatggcctctagcctggaggcttgctgaaggctgtatgctgttgagtttc gcattcttgttgccgttttggcctctgactgacggcaacaagagcgaaactcaacaggacacaaggcctgttactagcactcacatggaaca aatggcctctagcctggaggcttgctgaaggctgtatgctgtatcctcttataactcagcctccgtttttggcctctgactgacggaggctgagat aagaggatacaggacacaaggcctgttactagcactcacatggaacaaatggcctctctagaat

3'

SEQ ID NO: 17 = SEQ ID NO: 1 + SEQ ID NO: 9
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactctttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccttagggttccgatttagtgctttacggcacctcga ccccaaaaaacttgattagggtgatggttcacgtagtgggccatcgccctgatagacggtttttcgccctttgacgttggagtccacgttctttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcaccgtttgaatctttacctacacattactcaggcattgcatttaaaatatatgagggttctaaaaattttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa -continued

```
cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttttgctcacccagaaacgctggtgaaagtaaaagat gctgaagatcagttgggtgcacgagtgggttacatcgaactggatctcaacagcggtaagatccttgagagttttcgccccgaagaacgttttt ccaatgatgagcactttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgg gtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccaccccaattttgtatttatttattttttaattattttgtgcagcgatgggggggggggggggggggcgcgcgccaggc ggggggggggggcgagggggggggcggggcgaggcggagaggtgcggcggcagccaatcagagcggcgcgctccgaaagttt cctttttatggcgaggcggcggcggcggcggcccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtcgtactgacttgtaggtatgccgtttttggcctctgactgacggcataaaccctaagtcagt
```

-continued acgtcaggacacaaggcctgttactagcactcacatggaacaaatggcctctagcctggaggcttgctgaaggctgtatgctgactcctaat caatagcttccaccgttttggcctctgactgacggtggaagcttgattaggagtcaggacacaaggcctgttactagcactcacatggaacaa atggcctctagcctggaggcttgctgaaggctgtatgctgaatatgcctttaagctttgctgcgttttggcctctgactgacgcagcaaagcaa aggcatattcaggacacaaggcctgttactagcactcacatggaacaaatggcctctctagaat

3'

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 10-17 or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR. CASI promoter, miRNA expression cassette. WPRE. SV40 polyA and ITR 3'.

The invention claimed is:

1. A composition that comprises a recombinant plasmid (RP) comprising a sequence of nucleotides that is SEQ ID NO: 13.

2. The composition of claim 1, wherein the RP is encapsulated in a protein coat, a lipid vesicle, or any combination thereof.

* * * * *

SEQUENCE LISTING

Sequence total quantity: 17
SEQ ID NO: 1              moltype = DNA   length = 5883
FEATURE                   Location/Qualifiers
source                    1..5883
                          mol_type = other DNA
                          organism = synthetic construct
SEQUENCE: 1
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctctctta tgaggagttg 180
tggcccgttg tcaggcaacg tggcgtggtg tgcactgtgt ttgctgacgc aaccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc taagcttatc 600
gataccgtcg agatctaact tgtttattgc agcttataat ggttacaaat aaagcaatag 660
catcacaaat ttcacaaata aagcattttt ttcactgcat tctagttgtg gtttgtccaa 720
actcatcaat gtatcttatc atgtctggat ctcgacctcg actagagcat ggctacgtag 780
ataagtagca tggcgggtta atcattaact acaaggaacc cctagtgatg gagttggcca 840
ctccctctct gcgcgctcgc tcgctcactg aggccggggc accaaaggtc gcccgacgcc 900
cgggctttgc ccgggcggcc tcagtgagcg agcgagcgcg cagctggcgt aatagcgaag 960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gtattgcgac aacgttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg cgcagcgtga ccgctacact 1380
tgccagcgc ctagcgcccg ctcctttcgc tttcttccct tcctttctcg ccacgttcgc 1440
cggctttccc cgtcaagctc taaatcgggg ctccctttca gggttccgat ttagtgcttt 1500
acggcacctc gaccccaaaa aacttgatta gggtgatggt tcacgtagtg ggccatcgcc 1560

-continued

```
ctgatagacg gttttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggctttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc cttttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgttttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctattttat aggttaatgt  2520
catgataata atggtttctt agacgtcagg tggcactttt cggggaaatg tgcgcggaac  2580
ccctatttgt ttattttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cactttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccagggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggcctttttt  4320
acggttcctg gccttttgct ggccttttgc tcacatgttc tttcctgcgt tatccctga  4380
ttctgtggat aaccgtatta ccgcctttga gtgagctgat accgctcgcc gcagccgaac  4440
gaccgagcgc agcgagtcag tgagcgagga gcggaagag cgcccaatac gcaaaccgcc  4500
tctccccgcg cgttggccga ttcattaatg cagcagctgc gcgctcgctc gctcactgag  4560
gccgcacggc caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccaccccc aattttgtat ttatttattt tttaattatt ttgtgcagcg atggggggcgg  5160
ggggggggg gggcgcgcgc caggcggggc ggggcggggc gagggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actaccgcg ttactaaaac aggtaagtcc ggcctccgcg ccgggtttt gcgcctcccg  5460
cgggcgcccc cctcctcacg cgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacatttttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa caggtaccg ccaccatggc caccggctct  5820
cgcacaagcc tgctgctggc tttcggactg ctgtgcctgc cttggctcca ggagggctcc  5880
gcc                                                                    5883
```

```
SEQ ID NO: 2            moltype = DNA   length = 456
FEATURE                 Location/Qualifiers
source                  1..456
                        mol_type = other DNA
                        organism = synthetic construct
```

```
SEQUENCE: 2
gctagcatcg ataccgtcgc tatgtgctgg aggcttgctg aaggctgtat gctgtaaggt    60
ggttatggga gaatgccgtt ttggcctctg actgacggca ttctcctaac caccttacag   120
gacacaaggc ctgttactag cactcacatg gaacaaatgg cctctagcct ggaggcttgc   180
tgaaggctgt atgctgttga gtttcgcatt cttgttgccg ttttggcctc tgactgacgg   240
caacaagagc gaaactcaac aggacacaag gcctgttact agcactcaca tggaacaaat   300
ggcctctagc ctggaggctt gctgaaggct gtatgctgtc tatcctttca agctagtcac   360
cgttttggcc tctgactgac ggtgactagc gaaaggatag acaggacaca aggcctgtta   420
ctagcactca catggaacaa atggcctctc tagaat                             456

SEQ ID NO: 3              moltype = DNA   length = 456
FEATURE                   Location/Qualifiers
source                    1..456
                          mol_type = other DNA
                          organism = synthetic construct
SEQUENCE: 3
gctagcatcg ataccgtcgc tatgtgctgg aggcttgctg aaggctgtat gctgaagtta    60
gcatgtgtcc cagaaccgtt ttggcctctg actgacgatg ctgggacatg ctaacttcag   120
gacacaaggc ctgttactag cactcacatg gaacaaatgg cctctagcct ggaggcttgc   180
tgaaggctgt atgctgagaa gaaaggtatc ccaattgccg ttttggcctc tgactgacgg   240
caattgggac ctttcttctc aggacacaag gcctgttact agcactcaca tggaacaaat   300
ggcctctagc ctggaggctt gctgaaggct gtatgctgta gtgtttccaa atactgcttg   360
cgttttggcc tctgactgac gcaagcagta tggaaacact acaggacaca aggcctgtta   420
ctagcactca catggaacaa atggcctctc tagaat                             456

SEQ ID NO: 4              moltype = DNA   length = 456
FEATURE                   Location/Qualifiers
source                    1..456
                          mol_type = other DNA
                          organism = synthetic construct
SEQUENCE: 4
gctagcatcg ataccgtcgc tatgtgctgg aggcttgctg aaggctgtat gctgtctgac    60
agtgatgtca tcctttcgtt ttggcctctg actgacgaaa ggatgatcac tgtcagacag   120
gacacaaggc ctgttactag cactcacatg gaacaaatgg cctctagcct ggaggcttgc   180
tgaaggctgt atgctgattt aggtcagatg gaaactgccg ttttggcctc tgactgacgg   240
gagtttccct gacctaaatc aggacacaag gcctgttact agcactcaca tggaacaaat   300
ggcctctagc ctggaggctt gctgaaggct gtatgctgag tgtatgctta acgtggactt   360
cgttttggcc tctgactgac gaagtccacg aagcatacac tcaggacaca aggcctgtta   420
ctagcactca catggaacaa atggcctctc tagaat                             456

SEQ ID NO: 5              moltype = DNA   length = 456
FEATURE                   Location/Qualifiers
source                    1..456
                          mol_type = other DNA
                          organism = synthetic construct
SEQUENCE: 5
gctagcatcg ataccgtcgc tatgtgctgg aggcttgctg aaggctgtat gctgatactt    60
cagcctgaat cgtgaccgtt ttggcctctg actgacggtc acgattggct gaagtatcag   120
gacacaaggc ctgttactag cactcacatg gaacaaatgg cctctagcct ggaggcttgc   180
tgaaggctgt atgctgactt cactcatatt gttccactcg ttttggcctc tgactgacga   240
gtggaacaat gagtgaagtc aggacacaag gcctgttact agcactcaca tggaacaaat   300
ggcctctagc ctggaggctt gctgaaggct gtatgctgta tattctacaa atcaccaggg   360
cgttttggcc tctgactgac gccctggtga tgtagaatat acaggacaca aggcctgtta   420
ctagcactca catggaacaa atggcctctc tagaat                             456

SEQ ID NO: 6              moltype = DNA   length = 456
FEATURE                   Location/Qualifiers
source                    1..456
                          mol_type = other DNA
                          organism = synthetic construct
SEQUENCE: 6
gctagcatcg ataccgtcgc tatgtgctgg aggcttgctg aaggctgtat gctgtataag    60
tccagtgaga agaaggcgtt ttggcctctg actgacgcct tcttctctgg acttatacag   120
gacacaaggc ctgttactag cactcacatg gaacaaatgg cctctagcct ggaggcttgc   180
tgaaggctgt atgctgctat catcaaatga gctgctgcgt tttggcctct gactgacgca   240
gcagctcttg atgatagtca ggacacaagg cctgttacta gcactcacat ggaacaaatg   300
gcctctagcc tggaggcttg ctgaaggctg tatgctgaag actgctggaa attctatggc   360
tgttttggcc tctgactgac gaccatagaa tccagcagtc tcaggacaca aggcctgtta   420
ctagcactca catggaacaa atggcctctc tagaat                             456

SEQ ID NO: 7              moltype = DNA   length = 457
FEATURE                   Location/Qualifiers
source                    1..457
                          mol_type = other DNA
                          organism = synthetic construct
SEQUENCE: 7
gctagcatcg ataccgtcgc tatgtgctgg aggcttgctg aaggctgtat gctgattagc    60
actggtgatt tccggctgtt ttggcctctg actgacgacc ggaaatccag tgctaatcag   120
gacacaaggc ctgttactag cactcacatg gaacaaatgg cctctagcct ggaggcttgc   180
```

-continued

```
tgaaggctgt atgctgattg agtttcgcat tcttgttgcc gttttggcct ctgactgacg   240
gcaacaagag cgaaactcaa caggacacaa ggcctgttac tagcactcac atggaacaaa   300
tggcctctag cctggaggct tgctgaaggc tgtatgctga ttgatcaggc aaacatagtc   360
ccgtttggc ctctgactga cgggactatg tgcctgatca atcaggacac aaggcctgtt   420
actagcactc acatggaaca aatggcctct ctagaat                           457

SEQ ID NO: 8           moltype = DNA   length = 456
FEATURE                Location/Qualifiers
source                 1..456
                       mol_type = other DNA
                       organism = synthetic construct
SEQUENCE: 8
gctagcatcg ataccgtcgc tatgtgctgg aggcttgctg aaggctgtat gctgtctgat    60
cgtggtgtta tttgggcgtt ttggcctctg actgacgccc aaataaccac gatcagacag   120
gacacaaggc ctgttactag cactcacatg gaacaaatgg cctctagcct ggaggcttgc   180
tgaaggctgt atgctgttga gtttcgcatt cttgttgccg ttttggcctc tgactgacg   240
caacaagagc gaaactcaac aggacacaag gcctgttact agcactcaca tggaacaaat   300
ggcctctagc ctggaggctt gctgaaggct gtatgctgta tcctcttata actcagcctc   360
cgttttggcc tctgactgac ggaggctgag ataagaggac acaggacaca aggcctgtta   420
ctagcactca catggaacaa atggcctctc tagaat                            456

SEQ ID NO: 9           moltype = DNA   length = 456
FEATURE                Location/Qualifiers
source                 1..456
                       mol_type = other DNA
                       organism = synthetic construct
SEQUENCE: 9
gctagcatcg ataccgtcgc tatgtgctgg aggcttgctg aaggctgtat gctgtcgtac    60
tgacttgtag gtatgccgtt ttggcctctg actgacggca tacctaagtc agtacgtcag   120
gacacaaggc ctgttactag cactcacatg gaacaaatgg cctctagcct ggaggcttgc   180
tgaaggctgt atgctgactc ctaatcaata gcttccaccg ttttggcctc tgactgacg   240
tggaagcttg attaggagtc aggacacaag gcctgttact agcactcaca tggaacaaat   300
ggcctctagc ctggaggctt gctgaaggct gtatgctgaa tatgccttta agctttgctg   360
cgttttggcc tctgactgac gcagcaaagc aaaggcatat tcaggacaca aggcctgtta   420
ctagcactca catggaacaa atggcctctc tagaat                            456

SEQ ID NO: 10          moltype = DNA   length = 6339
FEATURE                Location/Qualifiers
source                 1..6339
                       mol_type = other DNA
                       organism = synthetic construct
SEQUENCE: 10
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccgggt ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg ggctacgtag   780
ataagtagca tggcgggtta tcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggc taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg ctccctttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaacctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
```

```
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttattttct aaatacattc aaatatgtat ccgctcatga gacaataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccacccc aattttgtat ttatttattt tttaattatt ttgtgcagcg atggggggcgg   5160
gggggggggg gggcgcgcgc caggcggggc ggggcggggc gaggggcggg gcggggcgag   5220
gcggaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcg gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtaa   5940
ggtggttatg ggagaatgcc gttttggcct ctgactgacg gcattctcct aaccacctta   6000
caggacacaa ggcctgttac tagcactcac atggaacaaa tggcctctag cctggaggct   6060
tgctgaaggc tgtatgctgt tgagtttcgc attcttgttg ccgtttggc ctctgactga   6120
cggcaacaag agcgaaactc aacaggacac aaggcctgtt actagcactc acatggaaca   6180
aatggcctct agcctggagg cttgctgaag ctgtatgct gtctatcctt tcaagctagt   6240
caccgttttg gcctctgact gacggtgact agcgaaagga tagacaggac acaaggcctg   6300
ttactagcac tcacatggaa caaatggcct ctctagaat             6339
```

```
SEQ ID NO: 11          moltype = DNA   length = 6339
FEATURE                Location/Qualifiers
source                 1..6339
                       mol_type = other DNA
                       organism = synthetic construct
SEQUENCE: 11
aatcaacctc tggattacaa aatttgtgaa agattgactg gtattcttaa ctatgttgct   60
ccttttacgt tatgtggata cgctgcttta atgcctttgt atcatgctat tgcttcccgt   120
atggctttca ttttctcctc cttgtataaa tcctggttgc tgtctcttta tgaggagttg   180
```

```
tggcccgttg tcaggcaacg tggcgtggtg tgcactgtgt ttgctgacgc aaccccact   240
ggttggggca ttgccaccac ctgtcagctc ctttccggga ctttcgcttt cccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gtagtgcttt  1500
acggcacctc gaccccaaaa aacttgatta gggtgatggt tcacgtagtg ggccatcgcc  1560
ctgatagacg gttttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgttttggg tacaaccgat  2160
ttagctttat gctctgaggc tttattgctt aatttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcacttt cggggaaatg tgcgcggaac  2580
ccctatttgt ttatttttct aaatacattc aaatatgtat ccgctcatga dacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag acccccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagatacccta cagcgtgagc tatgagaaag cgccacgctt cccgaaggga aaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg gcggagcct atggaaaaac gccagcaacg cggccttttt  4320
acggttcctg gccttttgct ggccttttgc tcacatgttc tttcctgcgt tatccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagccggg gcgtcggggc acctttgagc ggcctgctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
```

-continued

```
atatgccaag tacgcccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tccccccct    5100
ccccacccc aattttgtat ttatttattt tttaattatt ttgtgcagcg atgggggcgg    5160
gggggggggg gggcgcgcgc caggcggggc ggggcggggc gaggggcggg gcggggcgag    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aaccccagta tcagcagaag gacattttag gacgggactt gggtgactct agggcactgg    5640
ttttcttcc agagagcgga acaggcgagg aaaagtagtc ccttctcggc gattctgcgg    5700
agggatctcc gtggggcggt gaacgccgat gatgcctcta ctaaccatgt tcatgtttc    5760
ttttttttc tacaggtcct gggtgacgaa cagggtaccg ccaccatggc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgaag    5940
ttagcatgtg tcccagaacc gtttggcct ctgactgacg gttctgggac atgctaactt    6000
caggacacaa ggcctgttac tagcactcac atggaacaaa tggcctctag cctggaggct    6060
tgctgaaggc tgtatgctga gaagaaaggt atcccaattg ccgttttggc ctctgactga    6120
cggcaattgg gacctttctt ctcaggacac aaggcctgtt actagcactc acatggaaca    6180
aatggcctct agcctggagg cttgctgaag gctgtatgct gtagtgtttc caaatactgc    6240
ttgcgttttg gcctctgact gacgcaagca gtatggaaac actacaggac acaaggcctg    6300
ttactagcac tcacatggaa caaatggcct ctctagaat                          6339

SEQ ID NO: 12       moltype = DNA   length = 6339
FEATURE             Location/Qualifiers
source              1..6339
                    mol_type = other DNA
                    organism = synthetic construct
SEQUENCE: 12
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
gttgcaatgg ctggcggtaa tattgttctg gatattacca gcaaggccga tagtttgagt    1080
tcttctactc aggcaagtga tgttattact aatcaaagaa gtattgcgac aacggttaat    1140
ttgcgtgatg gacagactct tttactcggt ggcctcactg attataaaaa cacttctcag    1200
gattctggcg taccgttcct gtctaaaatc cctttaatcg gcctcctgtt tagctcccgc    1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgcc ctagcgcccg ctcctttcgc tttcttccct tcctttctcg ccacgttcgc    1440
cggctttccc cgtcaagctc taaatcgggg gctcccttta gggttccgat ttagtgcttt    1500
acggcacctc gaccccaaaa aacttgatta gggtgatggt tcacgtagtg ggccatcgcc    1560
ctgatagacg gtttttcgcc ctttgacgtt ggagtccacg ttctttaata gtggactctt    1620
gttccaaact ggaacaacac tcaacctat ctcggtctat tcttttgatt tataagggat    1680
tttgccgatt tcggcctatt ggttaaaaaa tgagctgatt taacaaaat ttaacgcgaa    1740
ttttaacaaa atattaacgt ttacaattta atatttgct tatacaatct tcctgttttt    1800
ggggctttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt aaaatatat gagggttcta aaaatttta tccttgcgtt    2100
gaaataaagg cttctcccgc aaaagtatta cagggtcata atgtttttgg tacaaccgat    2160
ttagctttat gctctgaggc tttattgctt aattttgcta attctttgcc ttgcctgtat    2220
gatttattgg atgttggaat tcctgatgcg gtattttctc cttacgcatc tgtgcggtat    2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctatttttat aggttaatgt    2520
catgataata atggtttctt agacgtcagg tggcactttc ggggaaatg tgcgcggaac    2580
ccctatttgt ttatttttct aaatacattc aaatatgtat ccgctcatga acaataaac    2640
ctgataaatg cttcaataat attgaaaaag gaagagtatg agtattcaac atttccgtgt    2700
cgcccttatt cccttttttg cggcatttg ccttcctgtt tttgctcacc agaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
```

```
cactttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctcacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatcgttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccagggga  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggcctttttt  4320
acggttcctg gccttttgct ggccttttgc tcacatgttc tttcctgcgt tatcccctga  4380
ttctgtggat aaccgtatta ccgccttttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtga  4740
agttccgcgt tacataactt acggtaaatg gcccgcctgg ctgaccgccc aacgacccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgcccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccccc aattttgtat ttatttattt tttaattatt ttgtgcagcg atggggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggctttg gccctcccg  5460
cgggcgcccc cctcctcacg cgcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgtttttc  5760
ttttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctaaga tcgataccgt cgctatgtgc tggaggcttg ctgaaggctg tatgctgctt  5940
gacagtgatg tcatcctttc gtttttggcct ctgactgacg aaaggatgat cactgtcaga  6000
caggacacaa ggcctgttac tagcactcac atggaacaaa tggcctctag cctgaggct  6060
tgctgaaggc tgtatgctga tttaggtcag atggaaactc gcgttttggc ctctgactga  6120
cgcgagtttc cctgacctaa atcaggacac aaggcctgtt actagcactc acatggaaca  6180
aatggcctct agcctggagg cttgctgaag gctgtatgct gagtgtatgc ttaacgtgga  6240
cttcgttttg gcctctgact gacgaagtcc acgaagcata cactcaggac acaaggcctg  6300
ttactagcac tcacatggaa caaatggcct ctctagaat                           6339
```

```
SEQ ID NO: 13        moltype = DNA  length = 6339
FEATURE              Location/Qualifiers
source               1..6339
                     mol_type = other DNA
                     organism = synthetic construct
SEQUENCE: 13
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga cttttcgctt tcccctccct  300
attgccacgg cggaactcat cgccgcctgc cttcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcga accttcctte ccgcggcctg ctgccggctct ccgcggcctt tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg tttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
```

-continued

```
ctccctctct  gcgcgctcgc  tcgctcactg  aggccgggcg  accaaaggtc  gcccgacgcc    900
cgggctttgc  ccgggcggcc  tcagtgagcg  agcgagcgcg  cagctggcgt  aatagcgaag    960
aggcccgcac  cgatcgccct  tcccaacagt  tgcgcagcct  gaatggcgaa  tggcgattcc   1020
gttgcaatgg  ctggcggtaa  tattgttctg  gatattacca  gcaaggccga  tagtttgagt   1080
tcttctactc  aggcaagtga  tgttattact  aatcaaagaa  gtattgcgac  aacggttaat   1140
ttgcgtgatg  gacagactct  tttactcggt  ggcctcactg  attataaaaa  cacttctcag   1200
gattctggcg  taccgttcct  gtctaaaatc  cctttaatcg  gcctcctgtt  tagctcccgc   1260
tctgattcta  acgaggaaag  cacgttatac  gtgctcgtca  aagcaaccat  agtacgcgcc   1320
ctgtagcggc  gcattaagcg  cggcgggtgt  ggtggttacg  cgcagcgtga  ccgctacact   1380
tgccagcgcc  ctagcgcccg  ctcctttcgc  tttcttccct  tcctttctcg  ccacgttcgc   1440
cggctttccc  cgtcaagctc  taaatcgggg  gctcccttta  gggttccgat  ttagtgcttt   1500
acggcacctc  gaccccaaaa  aacttgatta  gggtgatggt  tcacgtagtg  ggccatcgcc   1560
ctgatagacg  gttttttcgcc  ctttgacgtt  ggagtccacg  ttctttaata  gtggactctt   1620
gttccaaact  ggaacaacac  tcaaccctat  ctcggtctat  tcttttgatt  tataagggat   1680
tttgccgatt  tcggcctatt  ggttaaaaaa  tgagctgatt  taacaaaaat  ttaacgcgaa   1740
ttttaacaaa  atattaacgt  ttacaattta  aatatttgct  tatacaatct  tcctgttttt   1800
ggggcttttc  tgattatcaa  ccggggtaca  tatgattgac  atgctagttt  tacgattacc   1860
gttcatcgat  tctcttgttt  gctccagact  ctcaggcaat  gacctgatag  cctttgtaga   1920
gacctctcaa  aaatagctac  cctctccggc  atgaatttat  cagctagaac  ggttgaatat   1980
catattgatg  gtgatttgac  tgtctccggc  ctttctcacc  cgtttgaatc  tttacctaca   2040
cattactcag  gcattgcatt  taaaatatat  gagggttcta  aaaattttta  tccttgcgtt   2100
gaaataaagg  cttctcccgc  aaaagtatta  cagggtcata  atgtttttgg  tacaaccgat   2160
ttagctttat  gctctgaggc  tttattgctt  aattttgcta  attctttgcc  ttgcctgtat   2220
gatttattgg  atgttggaat  tcctgatgcg  gtattttctc  cttacgcatc  tgtgcggtat   2280
ttcacaccgc  atatggtgca  ctctcagtac  aatctgctct  gatgccgcat  agttaagcca   2340
gccccgacac  ccgccaacac  ccgctgacgc  gccctgacgg  gcttgtctgc  tcccggcatc   2400
cgcttacaga  caagctgtga  ccgtctccgg  gagctgcatg  tgtcagaggt  tttcaccgtc   2460
atcaccgaaa  cgcgcgagac  gaaagggcct  cgtgatacgc  ctatttttat  aggttaatgt   2520
catgataata  atggtttctt  agacgtcagg  tggcactttt  cggggaaatg  tgcgcggaac   2580
ccctatttgt  ttatttttct  aaatacattc  aaatatgtat  ccgctcatga  gacaataacc   2640
ctgataaatg  cttcaataat  attgaaaaag  gaagagtatg  agtattcaac  atttccgtgt   2700
cgcccttatt  ccctttttttg  cggcattttg  ccttcctgtt  tttgctcacc  cagaaacgct   2760
ggtgaaagta  aaagatgctg  aagatcagtt  gggtgcacga  gtgggttaca  tcgaactgga   2820
tctcaacagc  ggtaagatcc  ttgagagttt  tcgccccgaa  gcagttttc  caatgatgag   2880
cactttaaa  gttctgctat  gtggcgcggt  attatcccgt  attgacgccg  ggcaagagca   2940
actcggtcgc  cgcatacact  attctcagaa  tgacttggtt  gagtactcac  cagtcacaga   3000
aaagcatctt  acggatggca  tgacagtaag  agaattatgc  agtgctgcca  taaccatgag   3060
tgataacact  gcggccaact  tacttctgac  aacgatcgga  ggaccgaagg  agctaaccgc   3120
tttttttgcac  aacatggggg  atcatgtaac  tcgccttgat  cgttgggaac  cggagctgaa   3180
tgaagccata  ccaaacgacg  agcgtgacac  cacgatgcct  gtagcaatgg  caacaacgtt   3240
gcgcaaacta  ttaactggcg  aactacttac  tctagcttcc  cggcaacaat  taatagactg   3300
gatggaggcg  gataaagttg  caggaccact  tctgcgctcg  gcccttccgg  ctggctggtt   3360
tattgctgat  aaatctggag  ccggtgagcg  tgggtctcgc  ggtatcattg  cagcactggg   3420
gccagatggt  aagccctccc  gtatcgtagt  tatctacacg  acggggagtc  aggcaactat   3480
ggatgaacga  aatagacaga  tcgctgagat  aggtgcctca  ctgattaagc  attggtaact   3540
gtcagaccaa  gtttactcat  atatacttta  gattgattta  aaacttcatt  tttaatttaa   3600
aaggatctag  gtgaagatcc  tttttgataa  tctcatgacc  aaaatccctt  aacgtgagtt   3660
ttcgttccac  tgagcgtcag  accccgtaga  aaagatcaaa  ggatcttctt  gagatccttt   3720
ttttctgcgc  gtaatctgct  gcttgcaaac  aaaaaaacca  ccgctaccag  cggtggtttg   3780
tttgccggat  caagagctac  caactctttt  tccgaaggta  actggcttca  gcagagcgca   3840
gataccaaat  actgtccttc  tagtgtagcc  gtagttaggc  caccacttca  agaactctgt   3900
agcaccgcct  acatacctcg  ctctgctaat  cctgttacca  gtggctgctg  ccagtggcga   3960
taagtcgtgt  cttaccgggt  tggactcaag  acgatagtta  ccggataagg  cgcagcggtc   4020
gggctgaacg  gggggttcgt  gcacacagcc  cagcttggag  cgaacgacct  acaccgaact   4080
gagatacccta  cagcgtgagc  tatgagaaag  cgccacgctt  cccgaaggga  gaaaggcgga   4140
caggtatccg  gtaagcggca  gggtcggaac  aggagagcgc  acgagggagc  ttccaggggg   4200
aaacgcctgg  tatctttata  gtcctgtcgg  gtttcgccac  ctctgacttg  agcgtcgatt   4260
tttgtgatgc  tcgtcagggg  ggcggagcct  atggaaaaac  gccagcaacg  cggcctttttt   4320
acggttcctg  gccttttgct  ggccttttgc  tcacatgttc  tttcctgcgt  tatcccctga   4380
ttctgtggat  aaccgtatta  ccgcctttga  gtgagctgat  accgctcgcc  gcagccgaac   4440
gaccgagcgc  agcgagtcag  tgagcgagga  agcggaagag  cgcccaatac  gcaaaccgcc   4500
tctccccgcg  cgttggccga  ttcattaatg  cagcagctgc  gcgctcgctc  gctcactgag   4560
gccgcccggg  caaagcccgg  gcgtcgggcg  acctttggtc  gcccggcctc  agtgagcgag   4620
cgagcgcgca  gagagggagt  ggccaactcc  atcactaggg  gttccttgta  gttaatgatt   4680
aacccgccat  gctacttatc  tacgtagcca  tgctctagga  cattgattat  tgactagtgg   4740
agttccgcgt  tacataactt  acggtaaatg  gcccgcctgg  ctgaccgccc  aacgacccccc   4800
gcccattgac  gtcaataatg  acgtatgttc  ccatagtaac  gccaataggg  actttccatt   4860
gacgtcaatg  ggtggagtat  ttacggtaaa  ctgcccactt  ggcagtacat  caagtgtatc   4920
atatgccaag  tacgccccct  attgacgtca  atgacggtaa  atggcccgcc  tggcattatg   4980
cccagtacat  gaccttatgg  gactttccta  cttggcagta  catctacgta  ttagtcatcg   5040
ctattaccat  ggtcgaggtg  agccccacgt  tctgcttcac  tctccccatc  tcccccccct   5100
ccccacccc  aattttgtat  ttatttattt  tttaattatt  ttgtgcagcg  atggggggcgg   5160
ggggggggg  gggcgcgcgc  caggcggggc  ggggcggggc  gaggggcggg  gcggggcgag   5220
gcggagaggt  gcggcggcag  ccaatcagag  cggcgcgctc  cgaaagtttc  ctttatggc   5280
gaggcggcgg  cggcggcggc  cctataaaaa  gcgaagcgcg  cggcgggcgg  gagtcgctgc   5340
gcgctgcctt  cgccccgtgc  cccgctccgc  cgccgcctcg  cgccgcccgc  cccggctctg   5400
actgaccgcg  ttactaaaac  aggtaagtcc  ggcctccgcg  ccgggttttg  gcgcctcccg   5460
cgggcgcccc  cctcctcacg  gcgagcgctg  ccacgtcaga  cgaagggcgc  agcgagcgtc   5520
ctgatccttc  cgcccggacg  ctcaggacag  cggcccgctg  ctcataagac  tcggccttag   5580
```

```
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcgtgactg ctgtgcctgc cttggctcca ggagggctcc  5880
gccgctagca tcgataccgt cgctatgtgc tggaggcttg ctgaaggctg tatgctgata  5940
cttcagcctg aatcgtgacc gttttggcct ctgactgacg gtcacgattg gctgaagtat  6000
caggacacaa ggcctgttac tagcactcac atggaacaaa tggcctctag cctggaggct  6060
tgctgaaggc tgtatgctga cttcactcat attgttccac tcgtttttggc ctctgactga  6120
cgagtggaac aatgagtgaa gtcaggacac aaggcctgtt actagcactc acatggaaca  6180
aatggcctct agcctggagg cttgctgaag gctgtatgct gtatattcta caaatcacca  6240
gggcgttttg gcctctgact gacgccctgg tgatgtagaa tatacaggac acaaggcctg  6300
ttactagcac tcacatggaa caaatggcct ctctagaat                          6339
```

```
SEQ ID NO: 14            moltype = DNA  length = 6339
FEATURE                  Location/Qualifiers
source                   1..6339
                         mol_type = other DNA
                         organism = synthetic construct
SEQUENCE: 14
aatcaacctc tggattacaa aatttgtgaa agattgactg gtattcttaa ctatgttgct  60
cctttacgc tatgtggata cgctgcttta atgccttgt atcatgctat tgcttcccgt  120
atggctttca ttttctcctc cttgtataaa tcctggttgc tgtctctta tgaggagttg  180
tggcccgttg tcaggcaacg tggcgtggt tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctc  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc cttgggacgg cctccccgcc taagcttatc  600
gataccgtcg agatctaact tgtttattgc agcttataat ggttacaaat aaagcaatag  660
catcacaaat ttcacaaata aagcatttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaatc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa atattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctccctta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttcttttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggctttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt taaaatatat gagggttcta aaaatttta tccttgcgtt  2100
gaaataaagg cttctcccgc aaaagtatta cagggtcata atgttttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctattttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt ccctttttg cggcatttt ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cactttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
tttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatgaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
```

```
gtcagaccaa gtttactcat atatacttta gattgattta aaacttcatt tttaatttaa   3600
aaggatctag gtgaagatcc ttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcggat caaagcccgg cgtcgggcg acctttgtc gcccggcctc agtgagcga   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg cgagcgctg ccacgtcaga cgaagggcgc agcgagcgtc   5520
ctgatccttc cgcccggacg ctcaggacag cggcccggctg ctcataagac tcggccttag   5580
aaccccagta tcagcagaag gacatttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
ttttttttc tacaggtcct gggtgacgaa cagggtaccg ccaccatggc caccggctct   5820
cgcacaagcc tgctgctggc tttcggactg ctgtgcctgc cttggcttca ggagggctcc   5880
gccgctagca tcgataccgt cgctatgtgc tggaggcttg ctgaaggctg tatgctgtat   5940
aagtccagtg agaagaaggc gttttggcct ctgactgacg ccttcttctc tggacttata   6000
caggacacaa ggcctgttac tagcactcac atggaacaaa tggcctctag cctggaggct   6060
tgctgaaggc tgtatgctgc tatcatcaaa tgagctgctg cgttttggcc tctgactgac   6120
gcagcagctc ttgatgatag tcaggacaca aggcctgtta ctagcactcc catggaacaa   6180
atggcctcta gcctggaggc ttgctgaagg ctgtatgctg aagactgctg gaaattctat   6240
ggctgttttg gcctctgact gacgaccata gaatccagca gtctcaggac acaaggcctg   6300
ttactagcac tcacatggaa caaatggcct ctctagaat             6339
```

```
SEQ ID NO: 15          moltype = DNA   length = 6340
FEATURE                Location/Qualifiers
source                 1..6340
                       mol_type = other DNA
                       organism = synthetic construct
SEQUENCE: 15
aatcaacctc tggattacaa aatttgtgaa agattgactg gtattcttaa ctatgttgct   60
cctttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttc ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttt ttcactgcat tctagttgtg gtttgtccaa   720
actcatcaat gtatcttatc atgtctggat ctcgacctcg actagagcat ggctacgtag   780
ataagtagca tggcgggtta tcattaact acaaggaacc cctatgatg gagttggcca   840
ctccctctct gcgcgctcgc tcgctcactg aggccgcgg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctgcgcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt agctccccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
```

```
acggcacctc gaccccaaaa aacttgatta gggtgatggt tcacgtagtg ggccatcgcc   1560
ctgatagacg gttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggctttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta caggggtcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccce aattttgtat ttatttattt tttaattatt ttgtgcagcg atggggggcgg   5160
ggggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg cgagcgctg ccacgtcaga cgaagggcgc agcgagcgtc   5520
ctgatccttc cgcccggacg ctcaggacag cggccggctg ctcataagac tcggccttag   5580
aaccccagta tcagcagaag gacatttag gacgggactt gggtgactct agggcactgg   5640
tttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctacga tcgataccgt cgctatgtgc ctggaggctg ctgaaggctg tatgctgatt   5940
agcactggtg atttccggct gtttttggcct ctgactgacg accggaaatc cagtgctaat   6000
caggacacaa ggcctgttac tagcactcac atggaacaaa tggcctctag cctggaggct   6060
tgctgaaggc tgtatgctga ttgagtttcg cattcttgtt gccgttttgg cctctgactg   6120
acggcaacaa gagcgaaact caacaggaca caaggcctgt tactagcact cacatggaac   6180
aaatggcctc tagcctggag gcttgctgaa ggctgtatgc tgattgatca ggcaaacata   6240
```

```
gtcccgtttt ggcctctgac tgacgggact atgtgcctga tcaatcagga cacaaggcct  6300
gttactagca ctcacatgga acaaatggcc tctctagaat                         6340

SEQ ID NO: 16          moltype = DNA   length = 6339
FEATURE                Location/Qualifiers
source                 1..6339
                       mol_type = other DNA
                       organism = synthetic construct
SEQUENCE: 16
aatcaacctc tggattacaa aatttgtgaa agattgactg gtattcttaa ctatgttgct  60
cctttacgc tatgtggata cgctgcttta atgcctttgt atcatgctat tgcttcccgt   120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt cccctcccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc   600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc ccttaatcg gcctcctgtt tagctcccgc   1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gacccc aaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaattat cagctagaac ggttgaatat    1980
catattgatg tgatttgac tgtctccggc ctttctcacc cgtttgaatc tttacctaca    2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aatttttgct attctttgcc ttgcctgtat  2220
gatttattgg tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga caataaacc    2640
ctgataaatg cttcaataat attgaaaaag gaagagtatg agtattcaac atttccgtgt  2700
cgcccttatt ccttttttg cggcattttg ccttcctgtt tttgctcacc cagaaacgct   2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag   3060
tgataacact gcggccaact tacttctgac aacgatcgga ggaccgaagg agctaaccgc  3120
tttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acgggagtc aggcaactat    3480
ggatgaacga aatagacaga tcgctgagat aggtgcctca ctgattaagc attggtaact  3540
gtcagaccaa gtttactcat atatactttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga aaaggcgga   4140
caggtatccg gtaagcggca gggtcggaac aggagagcgc acgagggagc ttccaggggg  4200
```

```
aaacgcctgg tatctttata gtcctgtcgg gtttcgccac ctctgacttg agcgtcgatt    4260
tttgtgatgc tcgtcagggg ggcggagcct atggaaaaac gccagcaacg cggccttttt    4320
acggttcctg gccttttgct ggccttttgc tcacatgttc tttcctgcgt tatcccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagtgg    4740
agttccgcgt tacataactt acggtaaatg gcccgcctgg ctgaccgccc aacgaccccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tccccccct    5100
ccccacccc aattttgtat ttatttattt tttaattatt ttgtgcagcg atggggggcgg    5160
ggggggggg gggcgcgcgc caggcggggc ggggcgggc gaggggcggg gcggggcgag    5220
gcggagaggt gcggcggcag ccaatcagag cggcggctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aacccagta tcagcagaag gacattttag gacgggactt gggtgactct agggcactgg    5640
tttctttcc agagagcgga acaggcgagg aaaagtagtc ccttctcggc gattctgcgg    5700
agggatctgc gtggggcggt gaacgccgat gatgcctcta ctaaccatgt tcatgtttc    5760
tttttttttc tacaggtcct gggtgacgaa cagggtaccg ccaccatggc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgtct    5940
gatcgtggtg ttatttgggc gttttggcct ctgactgacg cccaaataac cacgatcaga    6000
caggacacaa ggcctgttac tagcactcac atggaacaaa tggcctctag cctggaggct    6060
tgctgaaggc tgtatgctgt tgagtttcgc attcttgttg ccgttttggc ctctgactga    6120
cggcaacaag agcgaaactc aacaggacac aaggcctgtt actagcactc acatggaaca    6180
aatggcctct agcctggagg cttgctgaag gctgtatgct gtatcctctt ataactcagc    6240
ctccgttttg gcctctgact gacggaggct gagataagag gatacaggac acaaggcctg    6300
ttactagcac tcacatggaa caaatggcct ctctagaat                           6339
```

SEQ ID NO: 17          moltype = DNA    length = 6339
FEATURE                  Location/Qualifiers
source                   1..6339
                           mol_type = other DNA
                           organism = synthetic construct

SEQUENCE: 17

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacga accccccact     240
ggttggggca ttgccaccac ctgtcagctc ctttccggga cttttcgctt tccccctccct     300
attgccacgg cggaactcat cgccgcctgc cttgcccgct gctggacagg ggctcggctg     360
ttgggcactg acaattccgt ggtgttgtcg gggaaatcat cgtcctttcc ttggctgctc     420
gcctgtggtg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc taagcttatc     600
gataccgtcg agatctaact tgtttattgc agcttataat ggttacaaat aaagcaatag     660
catcacaaat ttcacaaata aagcattttt ttcactgcat tctagttgtg gtttgtccaa     720
actcatcaat gtatcttatc atgtctggat ctcgacctcg actagagcat ggctacgtag     780
ataagtagca tggcgggtta atcattaact acaaggaacc cctagtgatg gagttggcca     840
ctccctctct gcgcgctcgc tcgctcactg aggccgggcg accaaggtc gcccgacgcc     900
cgggctttgc ccgggcggcc tcagtgagcg agcgagcgcg cagctggcgt aatagcgaag     960
aggcccgcac cgatcgccct tcccaacagt tgcgcagcct gaatgcgcaa tggcgattcc    1020
gttgcaatgg ctggcggtaa tattgttctg gatattacca gcaaggccga tagtttgagt    1080
tcttctactc aggcaagtga tgttattact aatcaaagaa gtattgcgac aacggttaat    1140
ttgcgtgatg acagactct tttactcggt ggcctcactg attataaaaa cacttctcag    1200
gattctggcg taccgttcct gtctaaaatc cctttaatcg gcctcctgtt tagctcccgc    1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgc ctagcgcccg ctcctttcgc tttcttccct tcctttctcg ccacgttcgc    1440
cggctttccc cgtcaagctc taaatcgggg gctccctta gggttccgat ttagtgcttt    1500
acggcacctc gaccccaaaa aacttgatta gggtgatggt tcacgtagtg ggccatcgcc    1560
ctgatagacg gtttttcgcc ctttgacgtt ggagtccacg ttctttaata gtggactctt    1620
gttccaaact ggaacaacac tcaacctat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaatatat gagggttcta aaaattttta tccttgcgtt    2100
gaaataaagg cttctcccgc aaaagtatta cagggtcata tgtttttgg tacaaccgat    2160
```

-continued

```
ttagctttat gctctgaggc tttattgctt aattttgcta attctttgcc ttgcctgtat    2220
gatttattgg atgttggaat tcctgatgcg gtatttctc cttacgcatc tgtgcggtat    2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctattttat aggttaatgt    2520
catgataata atggtttctt agacgtcagg tggcactttt cggggaaatg tgcgcggaac    2580
ccctatttgt ttattttct aaatacattc aaatatgtat ccgctcatga gacaataacc    2640
ctgataaatg cttcaataat attgaaaaag gaagagtatg agtattcaac atttccgtgt    2700
cgcccttatt ccctttttg cggcattttg ccttcctgtt tttgctcacc cagaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca    2940
actcggtcgc cgcatacact attctcagaa tgacttggtt gagtactcac cagtcacaga    3000
aaagcatctt acggatggca tgacagtaag agaattatgc agtgctgcca taaccatgag    3060
tgataacact gcggccaact tacttctgac aacgatcgga ggaccgaagg agctaaccgc    3120
tttttttgcac aacatggggg atcatgtaac tcgccttgat cgttgggaac cggagctgaa    3180
tgaagccata ccaaacgacg agcgtgacac cacgatgcct gtagcaatgg caacaacgtt    3240
gcgcaaacta ttaactggcg aactacttac tctagcttcc cggcaacaat taatagactg    3300
gatggaggcg gataaagttg caggaccact tctgcgctcg gcccttccgg ctggctggtt    3360
tattgctgat aaatctggag ccggtgagcg tgggtctcgc ggtatcattg cagcactggg    3420
gccagatggt aagccctccc gtatcgtagt tatctacacg acggggagtc aggcaactat    3480
ggatgaacga atagacaga tcgctgagat aggtgcctca ctgattaagc attggtaact    3540
gtcagaccaa gtttactcat atatacttta gattgattta aaacttcatt tttaatttaa    3600
aaggatctag gtgaagatcc tttttgataa tctcatgacc aaaatccctt aacgtgagtt    3660
ttcgttccac tgagcgtcag accccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg ggggttcgt gcacacagcc cagcttggag cgaacgacct acaccgaact    4080
gagataccta cagcgtgagc tatgagaaag cgccacgctt cccgaaggga gaaaggcgga    4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggcctttt    4320
acggttcctg gccttttgct ggccttttgc tcacatgttc tttcctgcgt tatcccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagaggggagt ggccaactcc atcactaggg gttccttgta gttaatgatt    4680
aacccgccat gctacttatc tacgtagcca tgctctagga cattgattat tgactagtag    4740
agttccgcgt tacataactt acggtaaatg gcccgcctgg ctgaccgccc aacgacccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tccccccct    5100
ccccacccc aattttgtat ttatttattt tttaattatt ttgtgcagcg atggggggcgg    5160
ggggggggg gggcgcgcgc caggcggggc ggggcggggc gaggggcggg gcgggggcag    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aaccccagta tcagcagaag gacattttag gacgggactt gggtgactct agggcactgg    5640
ttttctttcc agagagcgga acaggcgagg aaaagtagtc ccttctcggc gattctgcgg    5700
agggatctcc gtggggcggt gaacgccgat gatgcctcta ctaaccatgt tcatgtttc    5760
ttttttttc tacaggtcct gggtgacgaa cagggtaccg ccaccatggc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgtcg    5940
tactgacttg taggtatgcc gttttggcct ctgactgacg gcatacctaa gtcagtacgt    6000
caggacacaa ggcctgttac tagcactcac atggaacaaa tggcctctag cctggaggct    6060
tgctgaaggc tgtatgctga ctcctaatca atagcttcca ccgtttggc ctctgactga    6120
cggtggaagc ttgattagga gtcaggacac aaggcctgtt actagcactc acatggaaca    6180
aatggcctct agcctggagg cttgctgaag gctgtatgct gaatatgcct ttaagctttg    6240
ctgcgttttg gcctctgact gacgcagcaa agcaaaggca tattcaggac acaaggcctg    6300
ttactagcac tcacatggaa caaatggcct ctctagaat                          6339
```